(12) United States Patent
Baek et al.

(10) Patent No.: US 9,718,756 B2
(45) Date of Patent: *Aug. 1, 2017

(54) METHOD FOR CONTINUOUSLY RECOVERING (METH)ACRYLIC ACID AND APPARATUS FOR THE METHOD

(71) Applicant: LG CHEM, LTD., Seoul (KR)

(72) Inventors: Se Won Baek, Daejeon (KR); Jong Hun Song, Daejeon (KR); Sul Hee Yoo, Daejeon (KR); Yoon Jae Min, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,517

(22) PCT Filed: Jul. 8, 2014

(86) PCT No.: PCT/KR2014/006551
§ 371 (c)(1),
(2) Date: Jan. 7, 2016

(87) PCT Pub. No.: WO2015/012537
PCT Pub. Date: Jan. 29, 2015

(65) Prior Publication Data
US 2016/0145185 A1 May 26, 2016

(30) Foreign Application Priority Data

Jul. 23, 2013 (KR) .................. 10-2013-0086830
Aug. 30, 2013 (KR) .................. 10-2013-0104120
Sep. 17, 2013 (KR) .................. 10-2013-0112032

(51) Int. Cl.
*C07C 51/48* (2006.01)
*C07C 51/44* (2006.01)
(Continued)

(52) U.S. Cl.
CPC .............. *C07C 51/48* (2013.01); *B01D 3/143* (2013.01); *B01D 11/0484* (2013.01); *B01D 11/0488* (2013.01); *B01D 53/1418* (2013.01); *B01D 53/18* (2013.01); *C07C 51/43* (2013.01); *C07C 51/44* (2013.01); *C07C 51/16* (2013.01)

(58) Field of Classification Search
CPC ......... C07C 51/42; C07C 51/44; C07C 51/48; B01D 11/0488; B01D 11/0484;
(Continued)

(56) References Cited

U.S. PATENT DOCUMENTS 5,386,052 A 1/1995 Sakakura
5,872,288 A 2/1999 Haramaki et al.
(Continued)

FOREIGN PATENT DOCUMENTS

CN 1550489 A 12/2004
CN 1903738 A 1/2007
CN 101497563 A 8/2009
(Continued)

*Primary Examiner* — Yate K Cutliff
(74) *Attorney, Agent, or Firm* — Dentons US LLP

(57) ABSTRACT

This disclosure relates to a method of continuous recovery of (meth)acrylic acid and an apparatus used for the recovery method. The method of continuous recovery of (meth)acrylic acid according to the present invention may effectively remove scum formed in the continuous recovery process of (meth)acrylic acid, and simultaneously recover (meth)acrylic acid with excellent efficiency, thus enabling more stable operation of the continuous process.

13 Claims, 3 Drawing Sheets

(51) Int. Cl.
*B01D 3/14* (2006.01)
*B01D 11/04* (2006.01)
*B01D 53/14* (2006.01)
*B01D 53/18* (2006.01)
*C07C 51/43* (2006.01)
*C07C 51/16* (2006.01)

(58) Field of Classification Search
CPC .... B01D 53/18; B01D 53/1418; B01D 27/00; B01D 27/005; B01D 27/14
See application file for complete search history.

(56) References Cited

U.S. PATENT DOCUMENTS

| | | |
|---|---|---|
| 6,793,777 B1 | 9/2004 | Rudinger et al. |
| 2015/0203431 A1 | 7/2015 | Baek et al. |

FOREIGN PATENT DOCUMENTS

| | | |
|---|---|---|
| EP | 0117146 A1 | 8/1984 |
| JP | 56-79634 A | 6/1981 |
| JP | 08003112 A | 1/1996 |
| JP | 2000281617 A | 10/2000 |
| JP | 2001031624 A | 2/2001 |
| JP | 2001181233 A | 7/2001 |
| JP | 2003183221 A | 7/2003 |
| JP | 3769505 B2 | 2/2006 |
| JP | 2009263348 A | 11/2009 |
| JP | 2011225460 A | 11/2011 |
| KR | 1994-0021512 B2 | 10/1994 |
| KR | 10-0349602 B1 | 3/1999 |
| KR | 10-0371759 B1 | 5/2003 |
| KR | 10-0584677 B1 | 2/2005 |
| KR | 10-0888065 B1 | 3/2009 |
| KR | 10-2009-0041355 A | 4/2009 |
| KR | 10-2010-0107029 A | 10/2010 |
| KR | 10-2010-0112534 A | 10/2010 |
| KR | 10-1011769 B1 | 1/2011 |
| WO | 2013-037134 A1 | 3/2013 |

[Fig. 1]
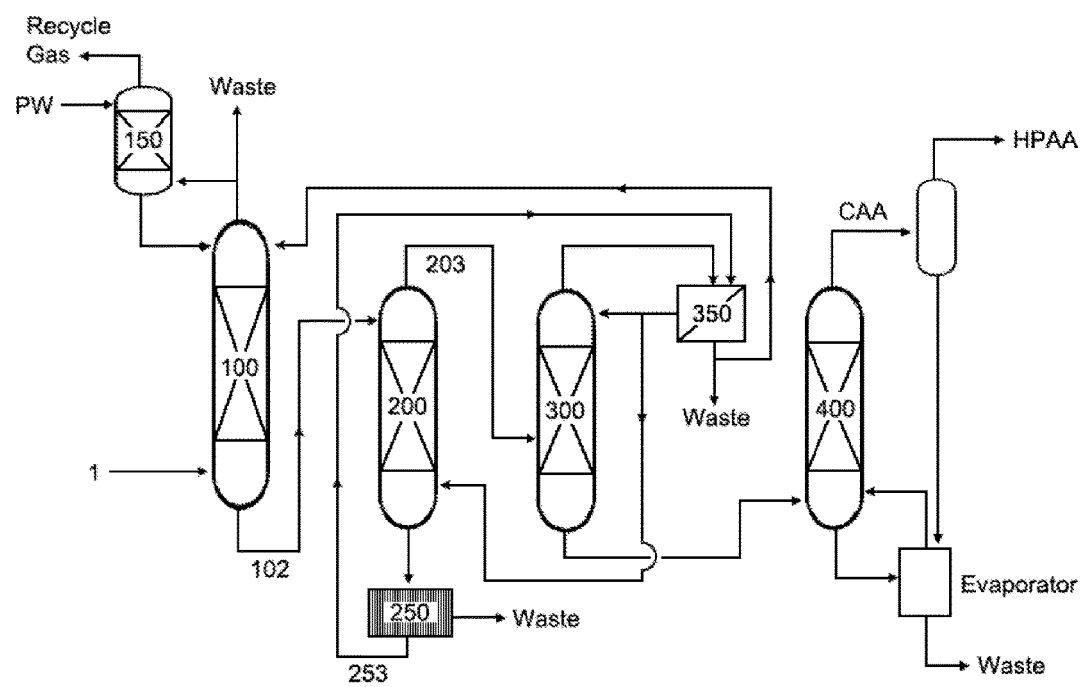

[Fig. 2]
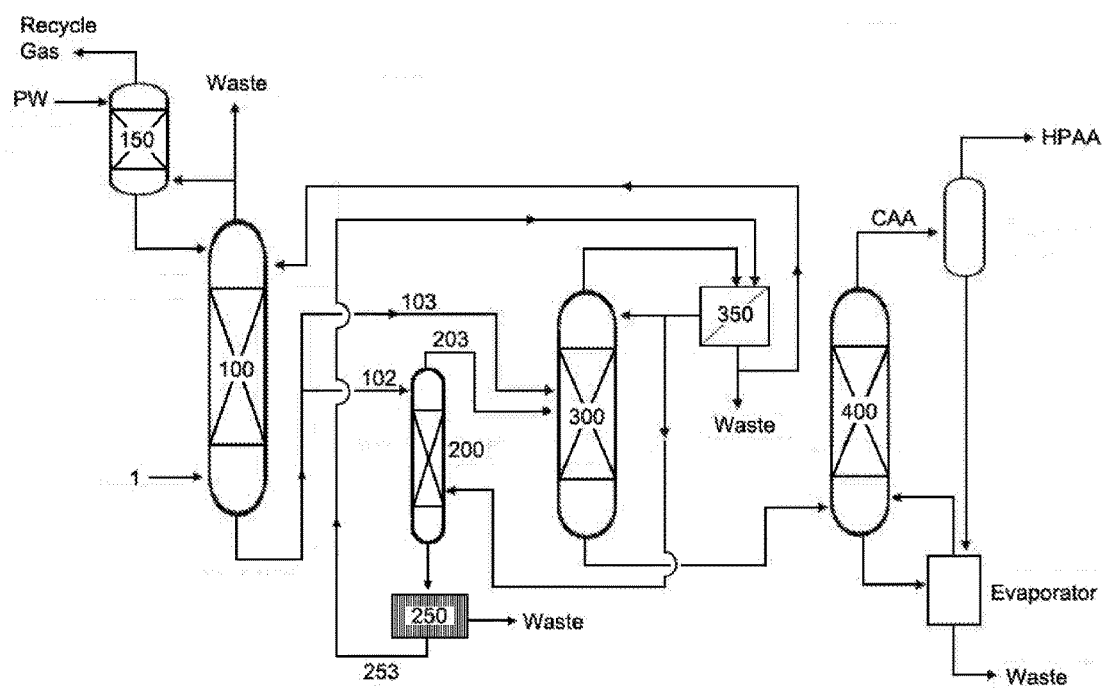

[Fig. 3]
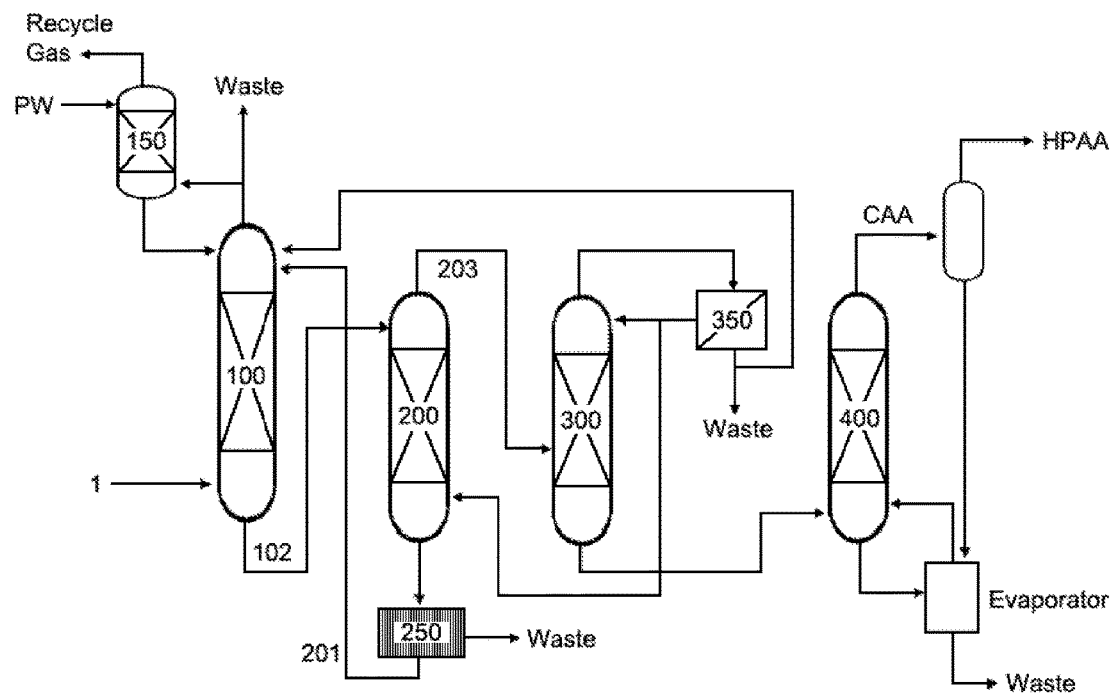

METHOD FOR CONTINUOUSLY RECOVERING (METH)ACRYLIC ACID AND APPARATUS FOR THE METHOD

This application is a National Stage Entry of International Application No. PCT/KR2014/006551, filed Jul. 18, 2014, and claims the benefit of and priority to Korean Application Nos. 10-2013-0086830, filed on Jul. 23, 2013, 10-2013-0104120, filed on Aug. 30, 2013, and 10-2013-0112032, filed on Sep. 17, 2013, all of which are hereby incorporated by reference in their entirety for all purposes as if fully set forth herein.

TECHNICAL FIELD

The present invention relates to a method of continuous recovery of (meth)acrylic acid and an apparatus for the method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, an inert gas, carbon dioxide, water vapor, and various organic by-products (acetic acid, heavies, and the like) is obtained in the back end of the reactor.

The (meth)acrylic acid-containing mixed gas contacts an absorption solvent including water in a (meth)acrylic acid absorption tower, and is recovered as a (meth)acrylic acid aqueous solution. Further, (meth)acrylic acid-stripped insoluble gas is recycled for a synthesis reaction of (meth)acrylic acid, and a part thereof is incinerated, converted into harmless gas, and discharged. The (meth)acrylic acid aqueous solution is extracted, distilled, and purified to obtain (meth)acrylic acid.

Meanwhile, various methods of controlling process conditions or a process sequence and the like to improve the recovery efficiency of (meth)acrylic acid have been suggested. Representatively, as a method for separating water and acetic acid from the (meth)acrylic acid aqueous solution obtained in the (meth)acrylic acid absorption tower, an azeotropic distillation method using a hydrophobic solvent in a distillation column is known. Further, a method of supplying a (meth)acrylic acid aqueous solution to an extraction column to obtain a (meth)acrylic acid extract solution with reduced water content and a raffinate solution thereof, and distilling the extract, thereby reducing energy consumption amount, is known.

Meanwhile, in the (meth)acrylic acid aqueous solution obtained in the (meth)acrylic acid absorption tower, in addition to (meth)acrylic acid, various organic by-products such as maleic acid, terephthalic acid, aldehyde, and (meth)acrylic acid polymer are included. Further, due to the properties of a continuous process for recovering (meth)acrylic acid, scum is formed due to poorly water-soluble materials in the organic by-products. The scum contaminates a (meth)acrylic acid recovery apparatus, and is particularly accumulated in an extraction column to lower recovery efficiency of (meth)acrylic acid, rendering long-time operation of the continuous process impossible.

Due to the properties of a continuous process, a possibility that solvents used in a (meth)acrylic acid extraction process and a distillation process or the organic by-products may be introduced into a (meth)acrylic acid absorption process or a (meth)acrylic acid synthesis process may not be excluded. Particularly, if the solvents or organic by-products are introduced into a (meth)acrylic acid synthesis process, a reactor and catalyst may be contaminated to lower reaction efficiency, and a serious stability problem may be caused.

DETAILED DESCRIPTION OF THE INVENTION

Technical Problem

It is an object of the present invention to provide a method of continuous recovery of (meth)acrylic acid that may more effectively remove scum produced in the continuous recovery process of (meth)acrylic acid, thus enabling stable operation of the continuous process.

It is another object of the present invention to provide an apparatus that can be used for the method of continuous recovery of (meth)acrylic acid.

Technical Solution

According to the present invention, provided is a method of continuous recovery of (meth)acrylic acid including an extraction process wherein a (meth)acrylic acid aqueous solution is contacted with an extraction solvent in an extraction column to obtain a (meth)acrylic acid extract solution and a raffinate solution, and a distilling process wherein feed containing the (meth)acrylic acid extract is distilled to obtain (meth)acrylic acid, wherein the raffinate solution produced in the extraction process remains stationary inside the extraction column and is then discharged, and the mass flow of the raffinate solution is controlled such that the amount of raffinate solution discharged from the extraction column is larger than the amount of raffinate solution produced by extraction, and the raffinate solution discharged from the extraction column is filtered to remove scum included in the raffinate solution.

Herein, the filtering of the raffinate solution may be conducted using a filter having pores with an average diameter of 50 µm or less.

The extraction solvent may be a hydrophobic solvent having a boiling point of 10 to 120° C.

Meanwhile, according to the present invention, the method of continuous recovery of (meth)acrylic acid may include: an absorption process wherein a mixed gas including (meth)acrylic acid, organic by-products, and water vapor, which is produced by a synthesis reaction of (meth)acrylic acid, is contacted with water to obtain a (meth)acrylic acid aqueous solution; an extraction process wherein the (meth)acrylic acid aqueous solution obtained through the absorption process is contacted with an extraction solvent in an extraction column to obtain a (meth)acrylic acid extract solution and a raffinate solution; and a distillation process wherein a feed including the (meth)acrylic acid extract obtained through the extraction process is distilled to obtain (meth)acrylic acid.

Further, according to the present invention, the method of continuous recovery of (meth)acrylic acid may include: an absorption process wherein a mixed gas including (meth)acrylic acid, organic by-products, and water vapor, which is produced by a synthesis reaction of (meth)acrylic acid, is contacted with water to obtain a (meth)acrylic acid aqueous solution; an extraction process wherein a part of the (meth) acrylic acid aqueous solution obtained through the absorption process is contacted with an extraction solvent in an extraction column to obtain a (meth)acrylic acid extract solution and a raffinate solution; and a distillation process wherein a feed including the remainder of the (meth)acrylic acid aqueous solution obtained through the absorption process and the (meth)acrylic acid extract solution obtained through the extraction process is distilled to obtain (meth) acrylic acid.

The filtrate from which scum has been removed through filtering of the raffinate solution may be separated into an aqueous phase and an organic phase by phase separation, the aqueous phase may be fed to the absorption process, and the organic phase may be fed to the distillation process.

The filtrate from which scum has been removed through filtering of the raffinate solution may be separated into an aqueous phase and an organic phase by phase separation, the aqueous phase may be fed to the absorption process, a part of the organic phase may be fed to the distillation process, and the remainder of the organic phase is fed to the extraction process.

Meanwhile, according to the present invention, provided is an apparatus for continuous recovery of (meth)acrylic acid, including:

a (meth)acrylic acid absorption tower (100) equipped with a mixed gas inlet to which a mixed gas including (meth) acrylic acid, organic by-products, and water vapor, which is produced by a synthesis reaction of (meth)acrylic acid, is fed, and an aqueous solution outlet from which a (meth) acrylic acid aqueous solution obtained by contact of the mixed gas with water is discharged;

a (meth)acrylic acid extraction column (200) equipped with an aqueous solution inlet connected with the aqueous solution outlet of the absorption tower (100) through an aqueous solution transfer line (102), an extract outlet from which (meth)acrylic acid extract solution obtained by contact of the introduced (meth)acrylic acid aqueous solution with an extraction solvent is discharged, and a raffinate outlet where the raffinate solution remains stationary and is then discharged;

a distillation column (300) equipped with an extract inlet connected with the extract outlet of the extraction column (200) through an extract transfer line (203), and a (meth) acrylic acid outlet from which (meth)acrylic acid obtained by distillation of the introduced extract solution is discharged; and a filtering system (250) equipped with a raffinate inlet connected with the raffinate outlet of the extraction column (200), a filter for filtering the introduced raffinate solution, a scum outlet from which scum separated from the raffinate solution by the filtering is discharged, and a filtrate outlet from which the filtrate is discharged, wherein the extraction column (200) is operated while controlling the mass flow of the raffinate solution such that the amount of raffinate solution discharged from the extraction column is larger than the amount of raffinate solution produced by extraction.

According to the present invention, the distillation column (300) is equipped with an aqueous solution inlet connected with the aqueous solution outlet of the absorption tower (100) through an aqueous solution transfer line (103), an extract inlet connected with the extract outlet of the extraction column (200) through an extract transfer line (203), and a (meth)acrylic acid outlet from which (meth) acrylic acid obtained by distillation of a mixture of the introduced aqueous solution and extract solution is discharged, wherein the apparatus may be operated such that a part of the (meth)acrylic acid aqueous solution discharged from the absorption tower (100) is fed to the extraction column (200), and the remainder of the (meth)acrylic acid aqueous solution is fed to the distillation column (300).

Herein, the filter of the filtering system (250) has pores with an average diameter of 50 μm or less.

The apparatus for continuous recovery of (meth)acrylic acid according to the present invention may include a phase separation tank (350) equipped with a filtrate inlet connected with the filtrate outlet of the filtering system (250) through a filtrate transfer line (253), and an aqueous phase outlet and an organic phase outlet from which an aqueous phase and an organic phase obtained by phase separation of the filtrate are respectively discharged, wherein the apparatus may be operated such that the aqueous phase is fed to the absorption tower (100), and the organic phase is fed to the distillation column (300).

In the apparatus for continuous recovery of (meth)acrylic acid according to the present invention, the filtrate outlet of the filtering system (250) may be connected with the upper part of the absorption tower (100) through a filtrate transfer line.

Advantageous Effects

The method of continuous recovery of (meth)acrylic acid according to the present invention may effectively remove scum formed in the continuous recovery process of (meth) acrylic acid, and simultaneously recover (meth)acrylic acid with excellent efficiency, thus enabling more stable operation of the continuous process.

BRIEF DESCRIPTION OF THE DRAWINGS

FIGS. 1 to 3 respectively schematically show the method and apparatus for continuous recovery of (meth)acrylic acid according to the embodiments of the invention.

REFERENCE NUMERALS

1: (meth)acrylic acid containing mixed gas
100: (meth)acrylic acid absorption tower
102: (meth)acrylic acid aqueous solution transfer line
150: acetic acid absorption tower
200: (meth)acrylic acid extraction column
203: extract transfer line
250: filtering system
253, 201: filtrate transfer line
300: distillation column
350: phase separation tank
400: high boiling point by-product separation tower
CAA: crude (meth)acrylic acid
HPAA: high purity (meth)acrylic acid

DETAILED DESCRIPTION OF THE EMBODIMENTS

Hereinafter, a method of continuous recovery of (meth) acrylic acid and a recovery apparatus according to the embodiments of the invention will be explained.

First, the technical terms used herein are only to mention specific embodiments, and are not intended to limit the invention. Further, singular forms used herein include plural forms, unless they have clearly opposite meanings. In addition, the meaning of 'comprising' as used herein embodies specific a property, area, integer, step, operation, element, or component, and it does not exclude the addition of other specific properties, areas, integers, steps, operations, elements, or components.

Unless otherwise described, terms used herein are defined as follows.

The term '(meth)acrylic acid' generally refers to acrylic acid, methacrylic acid, or a mixture thereof.

The term '(meth)acrylic acid-containing mixed gas' generally refers to a mixed gas that may be produced when (meth)acrylic acid is prepared by gas phase oxidation. As a non-limiting example, the (meth)acrylic acid-containing mixed gas may be obtained by gas phase oxidation of at least one compound selected from the group consisting of propane, propylene, butane, i-butylene, t-butylene, and (meth) acrolein ('raw material compound') in the presence of a catalyst, wherein the (meth)acrylic acid-containing mixed gas may include (meth)acrylic acid, non-reacted raw material compounds, (meth)acrolein, an inert gas, carbon monoxide, carbon dioxide, water vapor, and various organic by-products (acetic acid, heavies, and the like), and the like. Further, poorly water-soluble floating material formed by the organic by-products is referred to as 'scum'.

The term '(meth)acrylic acid aqueous solution' refers to an aqueous solution containing (meth)acrylic acid, and for example, it may be obtained by contacting the (meth)acrylic acid-containing mixed gas with an absorption solvent containing water.

The term 'feed' refers to a liquid mixture containing solute to be extracted, and it may be a mixture of a solute that is soluble in an extraction solvent and an inert material that is not soluble in an extraction solvent. Herein, if the extraction solvent is added to the feed, the solute is dissolved in the extraction solvent from the feed by mass transfer. Thereby, the extraction solvent in which a significant amount of solutes is dissolved forms an extract solution, and the feed that is deprived of a significant amount of solutes forms a raffinate solution.

Meanwhile, in liquid-liquid extraction using agitated columns such as a Karr-type column and a Scheibel-type column, a relatively light phase is fed to the lower stage of the extraction column, and a relatively heavy phase is fed to the upper stage of the extraction column. Extraction is progressed by the contact of materials fed to the extraction column, to obtain a light phase and a heavy phase of new compositions. The light phase of the new composition obtained through the extraction process is obtained through the upper outlet of the extraction column, and the heavy phase of the new composition is obtained through the lower outlet of the extraction column.

In general, the heavy phase of the new composition obtained through the extraction process, before being discharged to the lower outlet of the extraction column, remains stationary at the lower part of the extraction column, and a part thereof is discharged to the lower outlet of the extraction column. Herein, the section of the extraction column in which the heavy phase remains stationary is referred to as 'lower stationary section' (or 'stationary section of heavy phase'). For example, in the process of extracting (meth) acrylic acid included in a (meth)acrylic acid aqueous solution using an extraction solvent, the (meth)acrylic acid aqueous solution that is a relatively heavy phase is fed to the upper stage of the extraction column, and the extraction solvent that is a relatively light phase is fed to the lower stage of the extraction column. Further, extraction is progressed by the contact thereof, and an extract solution in which a significant amount of (meth)acrylic acid is dissolved and a raffinate solution that is deprived of a significant amount of (meth)acrylic acid are obtained.

Herein, the extract solution that is in a relatively light phase is obtained through the upper outlet of the extraction column, and the raffinate solution that is in a relatively heavy phase is obtained through the lower outlet of the extraction column. The raffinate solution, before being discharged to the lower outlet of the extraction column, remains stationary at the lower section of the extraction column, and a part thereof is discharged to the lower outlet of the extraction column. The section of the extraction column in which the raffinate solution remains stationary is referred to as 'lower stationary section' (or 'stationary section of raffinate solution'), and, in the raffinate solution, an organic phase and an aqueous phase exist together, while the raffinate solution may be separated into an organic phase and an aqueous phase and form an interface at the lower stationary section according to process conditions.

Hereinafter, referring to the attached drawings, specific embodiments of the invention will be explained in detail so that one of ordinary knowledge in the art may easily practice it. However, the present invention may be embodied in various forms, and is not limited to the examples.

In general, in the synthesis process of (meth)acrylic acid, various organic by-products are produced together with (meth)acrylic acid, and scum is formed by poorly water-soluble substances included in the organic by-products. Due to the characteristic of a continuous process, scum contaminates the inside of various apparatuses, thus making stable process operation impossible, and lowers recovery rate of (meth)acrylic acid.

In this regard, the inventors have suggested a method of continuous recovery of (meth)acrylic acid including an absorption process, an extraction process, and a distillation process, wherein the lower discharged material (raffinate solution) of the extraction column is filtered to remove scum, and the filtrate is used as an absorption solvent of the absorption process.

However, according to the study results of the inventors, it was confirmed that the previously suggested method can remove only a part of scum included in the raffinate solution, and thus, as the operation time elapses, scum is accumulated inside of the extraction column. Namely, scum is accumulated at the stationary section of a raffinate solution of the lower part of the extraction column (particularly, at the interface of the organic phase and the aqueous phase formed at the stationary section) while forming a layer, and as the operation time elapses, the thickness of accumulated scum increases from the interface respectively in the direction of the organic phase and the direction of the aqueous phase.

However, the previously suggested method selectively recovers and filters only the aqueous phase formed at the stationary section of the lower part of the extraction column, so as to use the filtrate as an absorption solvent of the absorption process of (meth)acrylic acid. Thus, according to the previously suggested method, among the scum accumulated at the interface, scum accumulated close to the aqueous phase can be removed, but scum accumulated close to the organic phase cannot be removed and remains. Thus, as the operation time elapses, scum is accumulated, and finally, shutdown of the extraction column becomes inevitable.

Further, due to the characteristic of a continuous process, a possibility that solvents used in the (meth)acrylic acid extraction process and distillation process or the organic by-products may be introduced in the (meth)acrylic acid absorption process or (meth)acrylic acid synthesis process cannot be eliminated. If the solvents or organic by-products are introduced in the absorption process or (meth)acrylic acid synthesis process, an absorption tower, a reactor, a reaction catalyst, and the like may be contaminated, recovery rate of (meth)acrylic acid may decrease, and a serious safety problem may be caused.

Thus, during the repeated studies of the inventors for ameliorating the problems, it was confirmed that if an extraction column is controlled such that an interface between an organic phase and an aqueous phase is not formed at the stationary section of a raffinate solution of the lower part of the extraction column (namely, among the organic phase and the aqueous phase, only a relatively light phase exists at the stationary section of a raffinate solution), accumulation of scum inside of the extraction column may be fundamentally blocked. Particularly, the blocking of accumulation of scum inside of the extraction column may be achieved by controlling the mass flow of the raffinate solution such that the amount of raffinate solution discharged from the extraction column ('discharged amount of raffinate solution') is larger than the amount of raffinate solution produced by extraction ('production amount of raffinate solution').

I. A Method of Continuous Recovery of (Meth)Acrylic Acid

According to one embodiment of the invention, a method of continuous recovery of (meth)acrylic acid is provided, including an extraction process wherein a (meth)acrylic acid aqueous solution is contacted with an extraction solvent in an extraction column to obtain a (meth)acrylic acid extract solution and a raffinate solution, and a distilling process wherein a feed containing the (meth)acrylic acid extract solution is distilled to obtain (meth)acrylic acid, wherein the raffinate solution produced in the extraction process remains stationary inside the extraction column and then is discharged, mass flow of the raffinate solution is controlled such that the amount of raffinate solution discharged from the extraction column is larger than the amount of raffinate solution produced by extraction, and the raffinate solution discharged from the extraction column is filtered to remove scum included in the raffinate solution.

Basically, the method of continuous recovery of (meth)acrylic acid includes an extraction process of a (meth)acrylic acid aqueous solution and a distillation process. Particularly, the method of continuous recovery of (meth)acrylic acid may block accumulation of scum inside of the extraction column, by controlling the mass flow of the raffinate solution such that the amount of raffinate solution discharged from the extraction column is larger than the amount of raffinate solution produced by extraction in the extraction process.

Specifically, at a steady state where stable operation is conducted, a raffinate solution that remains stationary at the stationary section of the lower part of the extraction column exists while an aqueous phase and an organic phase form an interface by phase separation. However, by controlling the mass flow of the raffinate solution such that the interface between the aqueous phase and the organic phase may not exist at the stationary section of the lower part of the extraction column, accumulation of scum inside the extraction column may be fundamentally blocked. Furthermore, by filtering the raffinate solution discharged to the lower part of the extraction column, most scum included in the raffinate solution may be more effectively removed, thus enabling more stable operation of the continuous process.

According to one embodiment of the invention, the method of continuous recovery of (meth)acrylic acid includes: an absorption process wherein a mixed gas including (meth)acrylic acid, organic by-products, and water vapor, which is produced by a synthesis reaction of (meth)acrylic acid, is contacted with water to obtain a (meth)acrylic acid aqueous solution; an extraction process wherein the (meth)acrylic acid aqueous solution obtained through the absorption process is contacted with an extraction solvent in an extraction column to obtain the (meth)acrylic acid extract solution and the raffinate solution; and a distillation process wherein a feed including the (meth)acrylic acid extract obtained through the extraction process is distilled to obtain (meth)acrylic acid. The method of continuous recovery of (meth)acrylic acid according to the first embodiment may be conducted using the apparatus shown in FIG. 1.

According to another embodiment of the invention, the method of continuous recovery of (meth)acrylic acid may include: an absorption process wherein a mixed gas including (meth)acrylic acid, organic by-products, and water vapor, which is produced by a synthesis reaction of (meth)acrylic acid, is contacted with water to obtain a (meth)acrylic acid aqueous solution; an extraction process wherein a part of the (meth)acrylic acid aqueous solution obtained through the absorption process is contacted with an extraction solvent in an extraction column to obtain a (meth)acrylic acid extract solution and a raffinate solution; and a distillation process wherein a feed including the remainder of the (meth)acrylic acid aqueous solution obtained through the absorption process and the (meth)acrylic acid extract solution obtained through the extraction process is distilled to obtain (meth)acrylic acid. The method of continuous recovery of (meth)acrylic acid according to the second embodiment may be conducted using the apparatus shown in FIG. 2.

Hereinafter, referring to FIG. 1 and FIG. 2, each process that can be included in the embodiments of the invention will be explained.

(Absorption Process)

An absorption process is a process for obtaining a (meth)acrylic acid aqueous solution, and it may be conducted by contacting the (meth)acrylic acid-containing mixed gas obtained through the synthesis reaction of (meth)acrylic acid with an absorption solvent including water.

As a non-limiting example, the synthesis reaction of (meth)acrylic acid may be conducted by the oxidation reaction of at least one compound selected from the group consisting of propane, propylene, butane, isobutylene, and (meth)acrolein in the presence of a gas phase catalyst. Herein, the gas phase oxidation reaction may be progressed using a gas phase oxidation reactor of a common structure and under common reaction conditions. As the catalyst for the gas phase oxidation reaction, common catalysts may be used, and for example, catalysts suggested in Korean Registered Patent No. 0349602 and No. 037818, and the like may be used. In the (meth)acrylic acid-containing mixed gas produced by the gas phase oxidation reaction, in addition to the desired product (meth)acrylic acid, non-reacted raw material compounds, intermediate (meth)acrolein, inert gas, carbon dioxide, vapor, and various organic by-products (acetic acid, light ends, heavies, and the like) may be included.

Further, referring to FIG. 1, the (meth)acrylic acid aqueous solution may be obtained by feeding a (meth)acrylic acid-containing mixed gas (1) to a (meth)acrylic acid absorption tower (100), to contact it with an absorption solvent including water.

Herein, the kind of the (meth)acrylic acid absorption tower (100) may be determined considering contact efficiency of the mixed gas (1) with the absorption solvent, and the like. As non-limiting examples, the (meth)acrylic acid absorption tower (100) may be a packed tower or a multistage tray tower. Inside the packed tower, a filler such as a Raschig ring, a pall ring, a saddle, gauze, structured packing, and the like may be applied.

Further, considering the efficiency of the absorption process, the mixed gas (1) may be fed to the lower part of the absorption tower (100), and the solvent including water may be fed to the upper part of the absorption tower (100).

The absorption solvent may include water such as tap water, deionized water, and the like, and it may include recycled process water introduced from other processes (for example, an aqueous phase recycled from an extraction process and/or a distillation process). In addition, in the absorption solvent, a trace amount of organic by-products introduced from other processes (for example, acetic acid) may be included. However, considering the absorption efficiency of (meth)acrylic acid, it is preferable that organic by-products may be included in the content of 15 wt % or less in the absorption solvent fed to the absorption tower (100) (particularly, in the recycled process water).

The (meth)acrylic acid absorption tower (100) may be operated at an internal pressure of 1 to 1.5 bar or 1 to 1.3 bar, and at an internal temperature of 50 to 100° C. or 50 to 80° C., considering condensation conditions and moisture content according to saturated water vapor pressure, and the like.

Meanwhile, in the absorption process, a (meth)acrylic acid aqueous solution is discharged to the lower part of the (meth)acrylic acid absorption tower (100), and (meth)acrylic acid-stripped non-condensable gas is discharged to the upper part thereof. Herein, it may be favorable in terms of the efficiency of the total process that 40 wt % or more, or 40 to 90 wt %, or 50 to 90 wt % of (meth)acrylic acid may be included in the (meth)acrylic acid aqueous solution.

The obtained (meth)acrylic acid aqueous solution, as shown in FIG. 1, may be fed to a (meth)acrylic acid extraction column (200) through an aqueous solution transfer line (102). Further, the obtained (meth)acrylic acid aqueous solution, as shown in FIG. 2, may be divided and fed to the (meth)acrylic acid extraction column (200) and a distillation column (300) through aqueous solution transfer lines (102 and 103).

As shown in FIG. 1, if an extraction process is introduced between a (meth)acrylic acid absorption process and a distillation process, most absorption solvent included in the (meth)acrylic acid aqueous solution may be removed in the extraction process, thus lowering a treatment load of the distillation process, and reducing energy consumption.

As shown in FIG. 2, if an extraction process is introduced between a (meth)acrylic acid absorption process and a distillation process, and simultaneously, a (meth)acrylic acid aqueous solution is divided and fed to the extraction process and the distillation process, the distillation process may be operated under more relaxed operation conditions than the process as shown in FIG. 1.

Herein, the ratio of the (meth)acrylic acid aqueous solution divided and fed to the extraction column (200) and the distillation column (300) may be determined considering capacity of each column, treatment performance, energy efficiency improvement effect, and the like. According to one embodiment, it may be favorable for manifestation of the above explained effect that 5 to 70 wt %, or 10 to 60 wt %, or 10 to 50 wt % of the (meth)acrylic acid aqueous solution may be fed to the extraction column (200), and the remainder may be fed to the distillation column (300).

Meanwhile, at least a part of the non-condensable gas discharged to the upper part of the (meth)acrylic acid absorption tower (100) may be fed to a process for recovering organic by-products (particularly, acetic acid) included in the non-condensable gas, and the remainder may be fed to a waste gas incinerator and discarded. Namely, according to one embodiment of the invention, a process of contacting the non-condensable gas with an absorption solvent to recover acetic acid included in the non-condensable gas may be progressed.

The process of contacting the non-condensable gas with an absorption solvent may be conducted in an acetic acid absorption tower (150). As a non-limiting example, an absorption solvent (process water) for absorbing acetic acid may be fed to the upper part of the acetic acid absorption tower (150), and an aqueous solution containing acetic acid may be discharged to the lower part of the acetic acid absorption tower (150). Further, the acetic acid-containing aqueous solution may be fed to the upper part of the (meth)acrylic acid absorption tower (100) and used as an absorption solvent, and acetic acid-stripped non-condensable gas may be recycled to the synthesis process of (meth)acrylic acid and reused.

Herein, for effective absorption of acetic acid, the acetic acid absorption tower (150) may be operated at the internal pressure of 1 to 1.5 bar or 1 to 1.3 bar, and at the internal temperature of 50 to 100° C. or 50 to 80° C. In addition, specific operation conditions of the acetic acid absorption tower (150) may follow the disclosure of Korean Laid-Open Patent Publication No. 2009-0041355.

(Extraction Process)

Meanwhile, an extraction process wherein a (meth)acrylic acid aqueous solution is contacted with an extraction solvent in an extraction column to obtain the (meth)acrylic acid extract solution and the raffinate solution is conducted. Herein, the (meth)acrylic acid aqueous solution may be prepared by the above-explained absorption process.

The extraction process may be conducted in a (meth)acrylic acid extraction column (200). The (meth)acrylic acid aqueous solution fed to the extraction column (200) contacts an extraction solvent, and is discharged as an extract solution in which a significant amount of (meth)acrylic acid is dissolved and a raffinate solution that is deprived of a significant amount of (meth)acrylic acid, respectively. Herein, the extraction solution that is a relatively light phase is obtained through the upper outlet of the extraction column (200), and the raffinate solution that is a relatively heavy phase is obtained through the lower outlet of the extraction column. Before the raffinate solution is discharged from the extraction column (200), a certain amount thereof remains stationary at the stationary section of the lower part of the extraction column, and a part thereof is discharged to the lower outlet of the extraction column.

As such, by contacting the (meth)acrylic acid aqueous solution with an extraction solvent in an extraction column (200) (namely, extraction with small energy consumption compared to distillation), most water included in the (meth)acrylic acid aqueous solution may be removed. Thereby, the treatment load of the subsequent distillation process may be lowered, thus improving energy efficiency of the total process. Furthermore, by lowering the treatment load of the distillation process, polymerization of (meth)acrylic acid that may be generated during distillation may be minimized, to secure more improved recovery efficiency of (meth)acrylic acid.

Meanwhile, in the case of a general extraction process, at the lower part of the extraction column, a certain amount of a raffinate solution remains stationary and exists while being phase separated into an organic phase and an aqueous phase.

Further, as the production amount of a raffinate solution by the extraction and the discharged amount of a raffinate solution through the lower outlet are maintained substantially the same, the amount of raffinate solution that remains stationary at the lower part of the extraction column and the interface between the organic phase and the aqueous phase are maintained at a constant level.

However, as the operation of the extraction column is continued, scum is accumulated at the interface between the organic phase and the aqueous phase due to the raffinate solution that remains stationary at the lower part of the extraction column. The scum is accumulated while forming a layer at the interface between the organic phase and the aqueous phase formed at the stationary section of the lower part of the extraction column, and as the operation progresses, the thickness of accumulated scum increases from the interface respectively toward the organic phase direction and the aqueous phase direction. However, since the scum contaminates various apparatuses, and particularly is accumulated at the extraction column to lower the recovery rate of (meth)acrylic acid, it is preferable to remove the scum for stable process operation.

With regard to removal of the scum, the inventors have suggested a method of removing scum by filtering a raffinate solution discharged to the lower part of the extraction column (200), and using the filtrate as an absorption solvent of an absorption process. However, according to the previously suggested method, among the scum accumulated at the interface between the organic phase and the aqueous phase, the scum close to the aqueous phase may be removed, but the scum close to the organic phase may not be removed and remains inside the extraction column. Thus, in the case of the previously suggested method, as the operation time elapses, scum is accumulated inside the extraction column, and finally, shut-down of the extraction column becomes inevitable.

However, in the method of continuous recovery of (meth)acrylic acid according to one embodiment, by controlling such that an interface between an organic phase and an aqueous phase may not be formed at the stationary section of a raffinate solution of the lower part of the extraction column (200) (namely, only a relatively light phase among the organic phase and the aqueous phase may exist at the stationary section of a raffinate solution), accumulation of scum inside the extraction column (200) may be fundamentally blocked. Particularly, the blocking of the accumulation of scum inside the extraction column (200) may be achieved by controlling the mass flow of a raffinate solution such that the amount of a raffinate solution discharged from the extraction column (discharged amount of a raffinate solution) is larger than the amount of a raffinate solution produced by extraction (production amount of a raffinate solution).

In addition, the method of continuous recovery of (meth)acrylic acid according to one embodiment may effectively remove scum included in the raffinate solution by filtering the raffinate solution discharged to the lower part of the extraction column (200), thus enabling more stable operation of the continuous process.

According to the embodiment of the invention, the production amount of a raffinate solution and the discharged amount of a raffinate solution in the extraction process may be controlled such that an interface between an organic phase and an aqueous phase may not be formed at the stationary section of a raffinate solution of the lower part of the extraction column (200), and only a relatively light phase may exist. Namely, at the stationary section of a raffinate solution of the lower part of the extraction column (200), the organic phase due to the phase separation of the raffinate solution is formed above the aqueous phase. Thus, the mass flow of the raffinate solution may be controlled such that the aqueous phase at the stationary section of a raffinate solution may be completely discharged, or a part of the organic phase may be discharged together with the aqueous solution.

Further, by additionally introducing the extraction solvent in the amount included in the raffinate solution discharged to the lower part of the extraction column (200), the weight ratio of the (meth)acrylic acid aqueous solution and the extraction solvent fed to the extraction column may be maintained at a constant level, thus maintaining stable extraction efficiency.

In addition, filtering of the raffinate solution may be conducted using a filter that can sufficiently remove scum included in the raffinate solution discharged from the extraction column (200). Thus, the filtering method of the raffinate solution and a filter used for the filtering are not specifically limited.

However, in order to obtain a substantial effect through filtering of the raffinate solution, it is preferable that 80 wt % or more, or 90 wt % or more of scum included in the raffinate solution may be removed by filtering. For this, filtering of the raffinate solution may be conducted using a filter having pores with an average diameter of 50 μm or less, or 0.1 to 30 μm, or 0.5 to 20 μm, or 0.5 to 10 μm. Namely, for sufficient removal of scum included in the raffinate solution, it is advantageous that a filter used for filtering may have pores with an average diameter of 50 μm or less. However, considering filtering efficiency, process flow, and the like, it is advantageous that the filter may have pores with an average diameter of 0.1 μm or more.

Further, although most raffinate solution discharged to the lower part of the extraction column (200) is in an aqueous phase, since an organic phase may be partly included, it is preferable that a filter used for filtering may be made of material having resistance to the extraction solvent, (meth)acrylic acid, and the like. As a non-limiting example, the filter may be made of cotton or a metal such as SUS (steel use stainless).

A filtering system (250) used for filtering of the raffinate solution may include at least one filter fulfilling the above requirement. Preferably, the filtering system (250) may have a structure wherein two or more filters having different average diameters are connected in series.

Most of the filtrate obtained through filtering of the raffinate solution may be in an aqueous phase, and an organic phase may be partly included. In case most of the filtrate is an aqueous solution, the filtrate may be fed as an absorption solvent of the above explained absorption process through a filtrate transfer line (201), as shown in FIG. 3. However, in case an organic phase unsuitable for use as an absorption solvent is included in the filtrate, it is preferable that the filtrate may be fed to a separate phase separation tank (350) through a filtrate transfer line (253) as shown in FIG. 1 or FIG. 2.

The aqueous phase obtained in the phase separation tank (350) may be fed to the absorption process as an absorption solvent, and the organic phase obtained in the phase separation tank (350) may be fed to the distillation process as an azeotropic solvent. Further, a part of the organic phase obtained in the phase separation tank (350) may be fed as an azeotropic solvent of the distillation process, and the remainder of the organic phase may be fed as an extraction solvent of the extraction process. However, in case an organic phase is divided and fed to the distillation process and the extraction process, it is a prerequisite that the same kind of solvent is used as the azeotropic solvent of the distillation process and the extraction solvent of the extraction process.

Meanwhile, it is preferable that the extraction solvent fed to the extraction column (200) may have solubility to (meth)acrylic acid and hydrophobicity. Further, considering the kind of solvent and the properties required in the subsequent distillation process, it is preferable that the extraction solvent may have a lower boiling point than (meth)acrylic acid. According to one embodiment of the invention, it is advantageous for process operation that the extraction solvent may be a hydrophobic solvent having a boiling point of 120° C. or less, or 10 to 120° C., or 50 to 120° C.

Specifically, the extraction solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

The feed amount of the extraction solvent may be controlled such that the weight ratio of the (meth)acrylic acid aqueous solution and the extraction solvent fed to the extraction column (200) may be 1:1 to 1:2, or 1:1.0 to 1:1.8, or 1:1.1 to 1:1.5, or 1:1.1 to 1:1.3. Namely, in order to secure appropriate extraction efficiency, it is preferable that the weight ratio of the (meth)acrylic acid aqueous solution and the extraction solvent fed to the extraction column (200) is maintained at 1:1 or more. Further, if the weight ratio exceeds 1:2, although extraction efficiency may be improved, loss of (meth)acrylic acid at a distillation column (300) of the subsequent process may increase, and reflux of an azeotropic solvent for preventing loss of (meth)acrylic acid may excessively increase, which is not preferable.

According to one embodiment of the invention, it is favorable for securing extraction efficiency that the temperature of the (meth)acrylic acid aqueous solution fed to the extraction column (200) may be 10 to 70° C.

As the extraction column (200), common extraction columns of a liquid-liquid contact type may be used without specific limitations. As non-limiting examples, the extraction column (200) may be a Karr-type reciprocating plate column, a rotary-disk contactor, a Scheibel column, a Kuhni column, a spray extraction tower, a packed extraction tower, a pulsed packed column, and the like.

Through the extraction process, a (meth)acrylic acid extract solution is discharged to the upper part of the extraction column (200), and the discharged extract solution is fed to a distillation column (300) through a transfer line (203). Further, a raffinate solution is discharged to the lower part of the extraction column (200), and the discharged raffinate solution is filtered through a filtering system (250) as explained above.

Herein, in the extract solution, in addition to the desired compound (meth)acrylic acid, an extraction solvent, water, and organic by-products may be included. As non-limiting examples, at a steady state where stable operation is conducted, 30 to 40 wt % of (meth)acrylic acid, 55 to 65 wt % of an extraction solvent, 1 to 5 wt % of water, and a remaining amount of organic by-products may be included in the extract solution. Namely, most water (for example, 85 wt % or more of water included in the aqueous solution) included in the (meth)acrylic acid aqueous solution may be recovered as a raffinate solution through the extraction process.

As most water is recovered from the extraction column (200), the distillation load of the distillation column (300) may be reduced to lower energy consumption. Further, since distillation conditions may be relaxed, polymerization of (meth)acrylic acid may be minimized in the distillation process, thus securing operation stability and improving recovery efficiency of (meth)acrylic acid.

In the raffinate solution discharged from the extraction column (200), non-extracted (meth)acrylic acid may be included. However, according to one embodiment of the invention, 5 wt % or less, or 0.5 to 5 wt %, or 1 to 3 wt % of (meth)acrylic acid may be included in the raffinate solution, thus minimizing the loss of (meth)acrylic acid in the absorption process and extraction process.

(Distillation Process)

A distillation process wherein a feed including the (meth)acrylic acid extract solution is distilled to obtain (meth)acrylic acid is conducted.

According to one embodiment of the invention, the feed may be a (meth)acrylic acid extract solution fed from the above-explained extraction process. In this case, the feed is fed to the distillation column (300) through the (meth)acrylic acid extract solution transfer line (203), as shown in FIG. 1.

Further, according to another embodiment, the feed may be a mixture of the (meth)acrylic acid aqueous solution fed from the above-explained absorption process and the (meth)acrylic acid extract solution fed from the above-explained extraction process. In this case, the feed may be simultaneously fed to the distillation column (300) through the (meth)acrylic acid aqueous solution transfer line (103) and the (meth)acrylic acid extract solution transfer line (203), as shown in FIG. 2.

Herein, for effective distillation, it is advantageous that a feed point to which the feed is supplied may be a central part of the distillation column (300), and preferably, it may be any one point corresponding to 40 to 60% of total stages from the uppermost stage of the distillation column (300).

As the feed supplied to the distillation column (300) contacts an azeotropic solvent introduced into the upper part of the distillation column (300), and is heated to an optimum temperature, distillation by evaporation and condensation is achieved.

Herein, in order to effectively separate (meth)acrylic acid included in the feed from the remaining components (for example, water, acetic acid, extraction solvents, and the like), the distillation is preferably conducted by azeotropic distillation.

A solvent used for the azeotropic distillation is preferably a hydrophobic azeotropic solvent that may form an azeotrope with water and acetic acid, and may not form an azeotrope with (meth)acrylic acid. Further, the hydrophobic azeotropic solvent preferably has a lower boiling point than (meth)acrylic acid (for example, a boiling point of 120° C. or less, or 10 to 120° C., or 50 to 120° C.).

Specifically, the hydrophobic azeotropic solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Particularly, in case the extraction process is introduced as in FIG. 1 and FIG. 2, considering production efficiency according to a continuous process, it is preferable that the hydrophobic azeotropic solvent is identical to the extraction solvent of the extraction process. As such, if the same kinds of solvents are used in the extraction process and the distillation process, at least a part of the solvent that is distilled in the distillation column (300) and recovered through the phase separation tank (350) may be fed to the (meth)acrylic acid extraction column (200) and reused as an extraction solvent.

Through the distillation process, among the feed, components other than (meth)acrylic acid are discharged to the upper part of the distillation column (300) together with the azeotropic solvent, and (meth)acrylic acid is discharged to the lower part of the distillation column (300).

The upper discharged solution of the distillation column (300) may be fed to the phase separation tank (350) and reused after a predetermined treatment. Herein, the phase separation tank (350) is an apparatus for separating immiscible liquids by gravity or centrifugal force and the like, wherein relatively light liquid (for example, an organic phase) may be recovered from the upper part of the phase separation tank (350), and relatively heavy liquid (for example, an aqueous phase) may be recovered from the lower part of the phase separation tank (350).

For example, the upper discharged solution of the distillation column (300) may be separated into an organic phase including an azeotropic solvent and an aqueous phase including water in the phase separation tank (350). Further, the filtrate obtained through filtering of the raffinate solution in the above-explained extraction process may be fed to the phase separation tank (350) through the filtrate transfer line (253) and phase separated together with the upper discharged solution of the distillation column (300). The separated organic phase may be fed to the upper part of the distillation column (300) and used as an azeotropic solvent. Further, if necessary, at least a part of the organic phase may be fed to the extraction column (200) and used as an extraction solvent. In addition, at least a part of the aqueous phase separated in the phase separation tank (350) may be fed to the (meth)acrylic acid absorption tower (100) and used as an absorption solvent, and a part thereof may be treated as waste water. Further, in the aqueous phase, acetic acid may be partly included, and the concentration of acetic acid included in the aqueous phase may vary according to the kind of azeotropic solvents and reflux ratio and the like. As non-limiting examples, the concentration of acetic acid included in the aqueous phase may be 1 to 50 wt %, or 2 to 40 wt %, or 3 to 30 wt %.

Meanwhile, while the (meth)acrylic acid aqueous solution passes through the (meth)acrylic acid absorption tower (100), extraction column (200), distillation column (300), and the like, at least a part of (meth)acrylic acid included in the aqueous solution may form dimers or oligomers. To minimize such polymerization of (meth)acrylic acid, common polymerization inhibitors may be added to the distillation column (300).

In the lower discharged solution of the distillation column (300), in addition to (meth)acrylic acid, heavies such as polymers of (meth)acrylic acid, polymerization inhibitors, and the like may be included. Thus, if necessary, a step of feeding the lower discharged solution of the distillation column (300) to a high boiling point by-product separation tower (400) and separating heavies included in the lower discharged solution may be further conducted. Further, crude (meth)acrylic acid (CAA) recovered through the process may be passed through an additional crystallization process and obtained as high purity (meth)acrylic acid (HPAA). Herein, the heavies separation process and the crystallization process and the like may be conducted under common conditions, and the process conditions are not specifically limited.

Meanwhile, in the method of continuous recovery of (meth)acrylic acid, each above-explained step may be conducted organically and continuously. Further, in addition to the above explained steps, processes that can be commonly conducted before or after or simultaneously with each step may be further included.

II. An Apparatus for Continuous Recovery of (Meth)Acrylic Acid

According to another embodiment of the invention, as shown in FIG. 1, an apparatus for continuous recovery of (meth)acrylic acid is provided, including:

a (meth)acrylic acid absorption tower (100) equipped with a mixed gas inlet to which a mixed gas including (meth)acrylic acid, organic by-products, and water vapor, which is produced by a synthesis reaction of (meth)acrylic acid, is fed, and an aqueous solution outlet from which a (meth)acrylic acid aqueous solution obtained by contact of the mixed gas with water is discharged;

a (meth)acrylic acid extraction column (200) equipped with an aqueous solution inlet connected with the aqueous solution outlet of the absorption tower (100) through an aqueous solution transfer line (102), an extract outlet from which the (meth)acrylic acid extract obtained by contact of the introduced (meth)acrylic acid aqueous solution with an extraction solvent is discharged, and a raffinate outlet where the raffinate solution remains stationary and then is discharged;

a distillation column (300) equipped with an extract inlet connected with the extract outlet of the extraction column (200) through an extract transfer line (203), and a (meth)acrylic acid outlet from which (meth)acrylic acid obtained by distillation of the introduced extract solution is discharged; and a filtering system (250) equipped with a raffinate inlet connected with the raffinate outlet of the extraction column (200), a filter for filtering the introduced raffinate solution, a scum outlet from which scum separated from the raffinate solution by the filtering is discharged, and a filtrate outlet from which the filtrate is discharged, wherein the extraction column (200) is operated while controlling the mass flow of the raffinate solution such that the amount of raffinate solution discharged from the extraction column is larger than the amount of raffinate solution produced by extraction.

According to yet another embodiment, as shown in FIG. 2, the distillation column (300) is equipped with an aqueous solution inlet connected with the aqueous solution outlet of the absorption tower (100) through an aqueous solution transfer line (103), an extract inlet connected with the extract outlet of the extraction column (200) through an extract transfer line (203), and a (meth)acrylic acid outlet from which (meth)acrylic acid obtained by distillation of a mixture of the introduced aqueous solution and extract is discharged, and the apparatus may be operated such that a part of the (meth)acrylic acid aqueous solution discharged from the absorption tower (100) is fed to the extraction column (200), while the remainder of the (meth)acrylic acid aqueous solution is fed to the distillation column (300).

In the apparatus according to the above embodiments, the (meth)acrylic acid absorption tower (100) may be a packed tower or a multistage tray tower for improving contact efficiency of the (meth)acrylic acid-containing mixed gas (1) with an absorption solvent including water. Inside of the packed tower, fillers such as a Raschig ring, a pall ring, a saddle, gauze, structured packing, and the like may be applied.

Further, as the (meth)acrylic acid extraction column (200), common extraction columns of a liquid-liquid contact type may be used without specific limitation. As non-limiting examples, the extraction column may be a Karr-type reciprocating plate column, a rotary-disk contactor), a Scheibel column, a Kuhni column, a spray extraction column, a packed extraction tower, a pulsed packed column, and the like.

Particularly, the filter of the filtering system (250) preferably has performance for sufficiently removing scum included in the raffinate solution discharged from the extraction column (200). Specifically, the filter may have pores with an average diameter of 50 μm or less, or 0.1 to 30 μm, or 0.5 to 20 μm, or 0.5 to 10 μm. Further, the filter is preferably made of a material having resistance to the extraction solvent and (meth)acrylic acid and the like, and as non-limiting examples, it may be made of cotton or a metal such as SUS (steel use stainless). In addition, the filtering system (250) used for filtering of the raffinate solution may include at least one filter fulfilling the above requirements. Preferably, the filtering system (250) may have a structure wherein two or more filters having pores with different average diameters are connected in series.

Meanwhile, the apparatus according to the above embodiments may include a phase separation tank (350) equipped with a filtrate inlet connected with the filtrate outlet of the filtering system (250) through a filtrate transfer line (253), and an aqueous phase outlet and an organic phase outlet from which an aqueous phase and an organic phase obtained by phase separation of the filtrate are respectively discharged. Herein, the apparatus may be operated such that the aqueous phase discharged from the phase separation tank (350) is fed to the absorption tower (100) and the organic phase is fed to the distillation column (300). Further, if necessary, the apparatus may be operated such that a part of the organic phase may be fed to the distillation column (300), and the remainder of the organic phase may be fed to the extraction column (200).

When most filtrate obtained in the filtering system (250) is in an aqueous phase, the filtrate outlet of the filtering system (250) may be connected to the upper part of the absorption tower (100) through a filtrate transfer line (201).

Further, the distillation column (300) may be a packed column including fillers inside or a multistage column, and preferably a sieve tray column, a dual flow tray column, and the like.

In addition, the acetic acid absorption tower (150), (meth) acrylic acid aqueous solution transfer line (102), extract solution transfer line (203), phase separation tank (350), high boiling point separation tower (400), and the like may have constructions common in the technical field to which the invention pertains.

Hereinafter, preferable examples are presented to aid in understanding of the invention. However, these examples are only to illustrate the invention, and the scope of the invention is not limited thereto.

Comparative Example 1

A Karr-type extraction column with an extraction part of a total of 52 stages and a total height of about 3 m was prepared. In the extraction column, the inner diameter of the column corresponding to the $1^{st}$ stage to the $6^{th}$ stage (namely, the upper 6 stages including the uppermost stage) was controlled to about 45 mm, and the inner diameter of the column corresponding to the remaining $7^{th}$ stage to $50^{th}$ stage was controlled to about 22 mm. Among the porous plates positioned at each stage of the extraction column and repeatedly moving up and down, the tray open area ratio of the porous plates positioned at the $1^{st}$ stage to the $6^{th}$ stage were controlled to about 50%, and the tray open area ratio of the porous plates positioned at the $7^{th}$ stage to the $50^{th}$ stage were controlled to about 28.3%.

To the feed inlet of the extraction column, an acrylic acid aqueous solution (acrylic acid concentration: about 65.5 wt %, acetic acid concentration: about 2.25 wt %) was fed, and toluene was fed to the extraction solvent inlet of the extraction column. Herein, the weight ratio of the acrylic acid aqueous solution to toluene fed to the extraction column was fixed to about 1:1.3.

At the lower stage of the extraction column from which the raffinate solution is discharged, a filtering system equipped with a cartridge type of filter having pores with an average diameter of about 10 μm was installed, and scum included in the raffinate solution discharged to the lower part of the extraction column was removed using the same.

Under maximum mechanical reciprocating speed of the porous plate (namely, maximum rpm immediately before generating flooding) enabling realization of a maximum acrylic acid extraction rate in the extraction column, the acrylic acid concentration in the raffinate solution was analyzed.

Herein, the input of the acrylic acid aqueous solution was controlled to 91.3 g/min, and the input of toluene was controlled to 115.8 g/min. Further, the discharge mass flow of the raffinate solution was controlled such that the interface of an organic phase and an aqueous phase formed by the raffinate solution that remains stationary at the lower part of the extraction column may be maintained at a constant level.

At the beginning of the operation, the mass flow of the raffinate solution was maintained at about 25.0 g/min and the interface was maintained at a constant level, but due to interface management failure during continued operation, the raffinate solution was discharged at about 30.6 g/min, which corresponds to about a 20% increase. Herein, in the raffinate solution in which an organic phase and an aqueous phase exist together in the emulsion form, acrylic acid concentration was about 1.17 wt %, and toluene concentration was about 13.6 wt %. The raffinate solution was inappropriate for use as an absorption solvent of the absorption process due to a high toluene concentration.

Comparative Example 2

To the feed inlet of an extraction column identical to that of Comparative Example 1, an acrylic acid aqueous solution (acrylic acid concentration: about 65.5 wt %, acetic acid concentration: about 2.25 wt %) was fed, and toluene was fed to the extraction solvent inlet of the extraction column. Herein, the weight ratio of the acrylic acid aqueous solution to toluene that were fed to the extraction column was fixed to about 1:1.3.

At the lower stage of the extraction column from which the raffinate solution is discharged, a filtering system equipped with a cartridge type of filter having pores with an average diameter of about 10 μm was installed, and scum included in the raffinate solution discharged to the lower part of the extraction column was removed using the same.

Herein, the input of the acrylic acid aqueous solution was controlled to 91.3 g/min, and the input of toluene was controlled to 118.1 g/min. Further, the discharge mass flow of the raffinate solution was maintained at about 25.0 g/min so that an interface between an organic phase and an aqueous phase formed by the raffinate solution that remains stationary at the lower part of the extraction column may be maintained at a constant level, wherein the discharge mass flow of the extract solution was about 184.4 g/min.

Under maximum mechanical reciprocating speed of the porous plate (namely, maximum rpm immediately before generating flooding) enabling realization of a maximum acrylic acid extraction rate in the extraction column, acrylic acid concentration in the raffinate solution was analyzed.

As the result, at the beginning of the operation, in a raffinate solution consisting of an aqueous phase, acrylic acid concentration was about 1.45 wt %, and toluene concentration was 720 ppm. Further, the mass flow of acrylic acid leaving as a raffinate solution was calculated as about 0.362 g/min.

However, at the stationary section of a raffinate solution of the lower part of the extraction column, scum was continuously accumulated at the interface between an organic phase and an aqueous phase due to phase separation of the raffinate solution. Further, as the operation of the extraction column was continued, scum was continuously accumulated toward the organic phase (namely, internal direction of the extraction column) at the interface between the organic phase and the aqueous phase at the stationary section of a raffinate solution of the lower part of the extraction column. Due to the accumulation of scum, the extraction column was contaminated, extraction efficiency gradually decreased, and finally, operation of the extraction column was stopped.

Example 1

A Karr type of extraction column with an extraction part of a total of 52 stages and a total height of about 3 m was prepared. In the extraction column, the inner diameter of the column corresponding to the $1^{st}$ stage to the $6^{th}$ stage (namely, the upper 6 stages including the uppermost stage) was controlled to about 45 mm, and the inner diameter of the column corresponding to the remaining $7^{th}$ stage to $50^{th}$ stage was controlled to about 22 mm. Among the porous plates positioned at each stage of the extraction column and repeatedly moving up and down, the tray open area ratio of the porous plates positioned at the $1^{st}$ stage to the $6^{th}$ stage were controlled to about 50%, and the tray open area ratio of the porous plates positioned at the $7^{th}$ stage to the $50^{th}$ stage were controlled to about 28.3%.

To the feed inlet of the extraction column, an acrylic acid aqueous solution (acrylic acid concentration: about 65.5 wt %, acetic acid concentration: about 2.25 wt %) was fed, and toluene was fed to the extraction solvent inlet of the extraction column. Herein, the weight ratio of the acrylic acid aqueous solution to toluene that were fed to the extraction column was fixed to about 1:1.3.

At the lower stage of the extraction column from which the raffinate solution is discharged, a filtering system equipped with a cartridge type of filter having pores with an average diameter of about 10 μm was installed, and scum included in the raffinate solution discharged to the lower part of the extraction column was removed using the same.

Herein, the input of the acrylic acid aqueous solution was controlled to 91.3 g/min, and the input of toluene was controlled to 115.8 g/min. Further, the mass flow of the raffinate solution was maintained at about 30.6 g/min so that an interface between an organic phase and an aqueous phase may not exist by the raffinate solution that remains stationary at the lower part of the extraction column.

The raffinate solution obtained through the lower outlet of the extraction column was passed through the filtering system to remove scum. In the filtrate in which an organic phase and an aqueous phase exist together in the emulsion form, acrylic acid concentration was about 1.17 wt %, and toluene concentration was about 13.6 wt %.

Further, the filtrate was fed to a phase separation tank, and phase-separated into an organic phase and an aqueous phase together with distillate of a distillation column. Herein, in the aqueous phase obtained from the separation tank, about 0.72 wt % of acrylic acid and about 730 ppm of toluene were included. Namely, it was confirmed that in the aqueous phase obtained in the phase separation tank, most toluene was removed compared to the raffinate solution obtained in the extraction column of Comparative Example 1, and acrylic acid was partly removed, and thus the aqueous phase was sufficient for use as an absorption solvent of an acrylic acid absorption process.

Example 2

A Karr type of extraction column with an extraction part of a total of 52 stages and a total height of about 3 m was prepared. In the extraction column, the inner diameter of the column corresponding to the $1^{st}$ stage to the $6^{th}$ stage (namely, the upper 6 stages including the uppermost stage) was controlled to about 45 mm, and the inner diameter of the column corresponding to the remaining $7^{th}$ stage to $50^{th}$ stage was controlled to about 22 mm. Among the porous plates positioned at each stage of the extraction column and repeatedly moving up and down, the tray open area ratio of the porous plates positioned at the $1^{st}$ stage to the $6^{th}$ stage were controlled to about 50%, and the tray open area ratio of the porous plates positioned at the $7^{th}$ stage to the $50^{th}$ stage were controlled to about 28.3%.

To the feed inlet of the extraction column, an acrylic acid aqueous solution (acrylic acid concentration: about 65.5 wt %, acetic acid concentration: about 2.25 wt %) was fed, and toluene was fed to the extraction solvent inlet of the extraction column. Herein, the weight ratio of the acrylic acid aqueous solution to toluene that were fed to the extraction column was fixed to about 1:1.3.

At the lower stage of the extraction column from which the raffinate solution is discharged, a filtering system equipped with a cartridge type of filter having pores with an average diameter of about 10 μm was installed, and scum included in the raffinate solution discharged to the lower part of the extraction column was removed using the same.

Herein, the input of the acrylic acid aqueous solution was controlled to 91.2 g/min, and the input of toluene was controlled to 123.6 g/min. Further, the mass flow of the raffinate solution was maintained at about 30.6 g/min so that an interface between an organic phase and an aqueous phase may not exist by the raffinate solution that remains stationary at the lower part of the extraction column, wherein the mass flow of an extract solution was 184.2 g/min.

The raffinate solution obtained through the lower outlet of the extraction column was passed through the filtering system to remove scum, and the filtrate was fed to a phase separation tank and separated into an organic phase and an aqueous phase. Herein, in the aqueous phase separated from the filtrate, about 1.34 wt % of acrylic acid and about 750 ppm of toluene were included, and in the organic phase separated from the filtrate, about 0.1 wt % of acrylic acid was included. Further, total mass flow of acrylic acid in the filtrate was calculated as about 0.359 g/min.

This result shows that extraction efficiency of an equivalent level to the initial extraction efficiency of the extraction column according to Comparative Example 2 is maintained. Further, as the apparatus was operated so that an interface between an organic phase and an aqueous phase may not exist at the stationary section of a raffinate solution of the lower part of the extraction column, the concentration of acrylic acid included in the raffinate solution did not increase even after operation for 7 or more days, enabling stable operation without accumulation of scum inside of the extraction column. Further, if differential pressure of the filtering system reaches a limit pressure, a filter is replaced or washed and reused, thereby enabling more stable long time operation of the extraction column.

The invention claimed is:

1. A method of continuous recovery of (meth)acrylic acid, comprising:
   an extraction step of contacting a (meth)acrylic acid aqueous solution with an extraction solvent in an extraction column to obtain a (meth)acrylic acid extract solution and a raffinate solution;
   a distilling step of distilling a feed containing the (meth)acrylic acid extract obtained in the extraction step to obtain (meth)acrylic acid, wherein the raffinate solution produced in the extraction step remains stationary inside the extraction column;
   a discharging step of discharging the stationary raffinate, wherein a mass flow of the raffinate solution is controlled such that an amount of raffinate solution discharged from the extraction column is larger than an amount of raffinate solution produced by extraction; and
   a filtration step of filtering the raffinate solution discharged from the extraction column to obtain a filtrate from which scum has been removed.

2. The method according to claim 1, wherein the filtration step is conducted using a filter having pores with an average diameter of 50 μm or less.

3. The method according to claim 1, wherein the extraction solvent is a hydrophobic solvent having a boiling point of 10 to 120° C.

4. The method according to claim 1, wherein the method further comprises:
   an absorption step of contacting a mixed gas comprising (meth)acrylic acid, organic by-products, and water vapor, which is produced by a synthesis reaction of (meth)acrylic acid, with water to obtain a (meth)acrylic acid aqueous solution, wherein the (meth)acrylic acid aqueous solution obtained from the absorption step is used in the extraction step.

5. The method according to claim 1, wherein the method further comprises:
   an absorption step of contacting a mixed gas comprising (meth)acrylic acid, organic by-products, and water vapor, which is produced by a synthesis reaction of (meth)acrylic acid, with water to obtain a (meth)acrylic acid aqueous solution,
   wherein a part of the (meth)acrylic acid aqueous solution obtained from the absorption step is contacted with the extraction solvent in the extraction step to obtain the (meth)acrylic acid extract solution and the raffinate solution, and
   wherein a remainder of the (meth)acrylic acid aqueous solution obtained from the absorption step is distilled in the distillation step to obtain the (meth)acrylic acid.

6. The method according to claim 4, further comprising:
   separating the filtrate from which scum has been removed into an aqueous phase and an organic phase by phase separation, and
   feeding the aqueous phase to the absorption step and feeding the organic phase to the distillation step.

7. The method according to claim 5, further comprising:
   separating the filtrate from which scum has been removed into an aqueous phase and an organic phase by phase separation, and
   feeding the aqueous phase to the absorption step, feeding a part of the organic phase to the distillation step, and feeding a remainder of the organic phase to the extraction step.

8. The method for continuous recovery of (meth)acrylic acid according to claim 4, wherein the synthesis reaction of (meth)acrylic acid is an oxidation reaction of at least one compound selected from the group consisting of propane, propylene, butane, isobutylene, and (meth)acrolein in the presence of a gas phase catalyst.

9. An apparatus for continuous recovery of (meth)acrylic acid, comprising:
   a (meth)acrylic acid absorption tower equipped with a mixed gas inlet to which a mixed gas including (meth)acrylic acid, organic by-products, and water vapor, which is produced by a synthesis reaction of (meth)acrylic acid, is fed, and an aqueous solution outlet from which a (meth)acrylic acid aqueous solution obtained by contact of the mixed gas with water is discharged;
   a (meth)acrylic acid extraction column equipped with an aqueous solution inlet connected with the aqueous solution outlet of the absorption tower through an aqueous solution transfer line, an extract outlet from which the (meth)acrylic acid extract obtained by contact of the introduced (meth)acrylic acid aqueous solution with an extraction solvent is discharged, and a raffinate outlet where the raffinate solution remains stationary and then is discharged;
   a distillation column equipped with an extract inlet connected with the extract outlet of the extraction column through an extract transfer line, and a (meth)acrylic acid outlet from which (meth)acrylic acid obtained by distillation of the introduced extract solution is discharged; and
   a filtering system equipped with a raffinate inlet connected with the raffinate outlet of the extraction column, a filter for filtering the introduced raffinate solution, a scum outlet from which scum separated from the raffinate solution by filtering is discharged, and a filtrate outlet from which the filtrate is discharged,
   wherein the apparatus is operated while controlling the mass flow of the raffinate solution such that the amount of raffinate solution discharged from the extraction column is larger than the amount of raffinate solution produced by extraction.

10. The apparatus for continuous recovery of (meth)acrylic acid according to claim 9, wherein the distillation column is equipped with an aqueous solution inlet connected with the aqueous solution outlet of the absorption tower through an aqueous solution transfer line, an extract inlet connected with the extract outlet of the extraction column through an extract transfer line, and a (meth)acrylic acid outlet from which (meth)acrylic acid obtained by distillation of a mixture of the introduced aqueous solution and extract is discharged, and the apparatus is operated such that a part of the (meth)acrylic acid aqueous solution discharged from the absorption tower is fed to the extraction column, and the remainder of the (meth)acrylic acid aqueous solution is fed to the distillation column.

11. The apparatus for continuous recovery of (meth)acrylic acid according to claim 9, wherein the filter of the filtering system has pores with an average diameter of 50 μm or less.

12. The apparatus for continuous recovery of (meth)acrylic acid according to claim 9, wherein the apparatus comprises a phase separation tank equipped with a filtrate inlet connected with the filtrate outlet of the filtering system through a filtrate transfer line, and an aqueous phase outlet and an organic phase outlet from which an aqueous phase and an organic phase obtained by phase separation of the filtrate are respectively discharged, and the apparatus is operated such that the aqueous phase is fed to the absorption tower and the organic phase is fed to the distillation column.

13. The apparatus for continuous recovery of (meth)acrylic acid according to claim 9, wherein the filtrate outlet of the filtering system is connected with the upper part of the absorption tower through a filtrate transfer line.

\* \* \* \* \*

UNITED STATES PATENT AND TRADEMARK OFFICE
CERTIFICATE OF CORRECTION

Page 1 of 1

PATENT NO. : 9,718,756 B2
APPLICATION NO. : 14/903517
DATED : August 1, 2017
INVENTOR(S) : Se Won Baek et al.

It is certified that error appears in the above-identified patent and that said Letters Patent is hereby corrected as shown below:

On the Title Page

The PCT filed date should read as below:
(22) PCT filed: Jul. 18, 2014

Signed and Sealed this
Twenty-fourth Day of October, 2017

Joseph Matal
*Performing the Functions and Duties of the
Under Secretary of Commerce for Intellectual Property and
Director of the United States Patent and Trademark Office*